(12) United States Patent
Podolsky

(10) Patent No.: US 7,538,082 B2
(45) Date of Patent: May 26, 2009

(54) METHODS AND COMPOSITIONS FOR TREATING ORAL AND ESOPHAGEAL LESIONS

(75) Inventor: Daniel K. Podolsky, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/434,752

(22) Filed: May 9, 2003

(65) Prior Publication Data

US 2003/0181383 A1    Sep. 25, 2003

Related U.S. Application Data

(63) Continuation-in-part of application No. 10/131,063, filed on Apr. 24, 2002, now abandoned.

(60) Provisional application No. 60/286,240, filed on Apr. 24, 2001, provisional application No. 60/422,708, filed on Oct. 31, 2002.

(51) Int. Cl.
*A01N 37/18* (2006.01)
(52) U.S. Cl. .......................................................... 514/2
(58) Field of Classification Search ...................... 514/2
See application file for complete search history.

(56) References Cited

U.S. PATENT DOCUMENTS

| | | | |
|---|---|---|---|
| 4,370,317 A | 1/1983 | Jorgensen et al. | |
| 5,541,210 A | 7/1996 | Cupps et al. | |
| 5,703,047 A | 12/1997 | Wilson | |
| 5,783,416 A | 7/1998 | Thim et al. | |
| 5,830,706 A | 11/1998 | Mascarenhas et al. | |
| 5,843,701 A | 12/1998 | Gold et al. | |
| 6,063,755 A | 5/2000 | Podolsky | |
| 6,221,840 B1 | 4/2001 | Podolsky | |
| 6,288,118 B1 | 9/2001 | Nieman | |
| 6,316,218 B1 | 11/2001 | Podolsky | |
| 6,426,404 B1 | 7/2002 | Podolsky | |
| 6,525,018 B1 | 2/2003 | Podolsky | |
| 6,685,917 B2* | 2/2004 | Rosenthal et al. | 424/49 |
| 6,984,628 B2 | 1/2006 | Bakhit et al. | |
| 7,220,418 B1 | 5/2007 | Hans et al. | |
| 2002/0052483 A1 | 5/2002 | Podolsky | |
| 2002/0119104 A1 | 8/2002 | Rosenthal et al. | 424/49 |
| 2002/0151472 A1 | 10/2002 | Thim et al. | |
| 2002/0187487 A1 | 12/2002 | Goldenring et al. | |
| 2003/0032585 A1 | 2/2003 | Thim et al. | |
| 2003/0077696 A1 | 4/2003 | Thim et al. | |
| 2003/0078205 A1 | 4/2003 | Podolsky | |
| 2003/0105016 A1 | 6/2003 | Podolsky | |
| 2003/0114384 A1 | 6/2003 | Podolsky | |
| 2003/0134797 A1 | 7/2003 | Podolsky | |
| 2003/0148949 A1 | 8/2003 | Podolsky | |
| 2003/0153496 A1 | 8/2003 | Thim et al. | 514/12 |
| 2003/0166535 A1 | 9/2003 | Podolsky | |
| 2003/0181383 A1 | 9/2003 | Podolsky | |
| 2003/0181384 A1 | 9/2003 | Podolsky | |
| 2003/0185838 A1 | 10/2003 | Podolsky | |
| 2003/0185839 A1 | 10/2003 | Podolsky | |
| 2003/0186880 A1 | 10/2003 | Podolsky | |
| 2003/0186882 A1 | 10/2003 | Podolsky | |
| 2003/0186886 A1 | 10/2003 | Podolsky | |
| 2003/0215431 A1 | 11/2003 | Thim et al. | 424/94.6 |
| 2003/0225250 A1 | 12/2003 | Podolsky | |
| 2004/0171544 A1 | 9/2004 | Barker et al. | |
| 2005/0287640 A1 | 12/2005 | Thim et al. | |
| 2006/0019881 A1 | 1/2006 | Thim et al. | |
| 2006/0046958 A1 | 3/2006 | Bakhit et al. | |
| 2006/0111278 A1 | 5/2006 | Thim et al. | |
| 2006/0188471 A1 | 8/2006 | Podolsky | |
| 2006/0189526 A1 | 8/2006 | Podolsky | |
| 2006/0211605 A1 | 9/2006 | Thim et al. | |
| 2006/0241037 A1 | 10/2006 | Olejnik et al. | |
| 2006/0293221 A1 | 12/2006 | Thim et al. | |
| 2007/0062517 A1 | 3/2007 | Barker | |
| 2007/0148733 A1 | 6/2007 | Woon et al. | |

FOREIGN PATENT DOCUMENTS

| | | |
|---|---|---|
| EP | 0 534 310 | 3/1993 |
| FR | 2769502 | 4/1999 |
| WO | WO 86/02271 | 4/1986 |
| WO | WO 92/14837 | 9/1992 |
| WO | WO 94/17102 | 8/1994 |
| WO | WO 96/06861 | 3/1996 |
| WO | WO 97/38712 | 10/1997 |
| WO | WO 98/30592 | 7/1998 |
| WO | WO 99/18927 | 4/1999 |

(Continued)

OTHER PUBLICATIONS

Rudinger et al, in "Peptide Hormones", edited by Parsons, J.A., University Park Press, Jun. 1976, p. 6.*

(Continued)

*Primary Examiner*—Patricia A Duffy
(74) *Attorney, Agent, or Firm*—Clark & Elbing LLP

(57) ABSTRACT

The invention features methods and compositions for treating or preventing lesions of the upper alimentary canal, particularly oral aphthous or mucositis lesions. Trefoil peptides are administered in effective concentrations either alone or in combination with different therapeutic agents.

20 Claims, 4 Drawing Sheets

FOREIGN PATENT DOCUMENTS

| | | |
|---|---|---|
| WO | WO 00/20868 | 4/2000 |
| WO | WO 00/74655 A2 | 12/2000 |
| WO | WO 01/02570 A1 | 1/2001 |
| WO | WO 01/29269 A2 | 4/2001 |
| WO | WO 02/46226 | 6/2002 |
| WO | WO 02/085402 A | 10/2002 |
| WO | WO 02/102399 | 12/2002 |
| WO | WO 02/102403 | 12/2002 |
| WO | WO 03/068817 | 8/2003 |
| WO | WO 2004/064860 | 8/2004 |
| WO | WO 2004/064860 A1 | 8/2004 |
| WO | WO 2005/009459 | 2/2005 |
| WO | WO 2005/039619 | 5/2005 |
| WO | WO 2005/039640 | 5/2005 |

OTHER PUBLICATIONS

Burgess et al., The Journal of Cell Biology, 111:2129-2138, 1990.*
Lazar et al., Molecular and Cellular Biology, 8(3):1247-1252, 1988.*
National Cancer Institute-Dictionary of Cancer.*
Life Sciences Dictionary.*
On-line Medical Dictionary.*
Dorland's Medical Dictionary.*
Bork et al, (Genome Research 10:398-400, 2000.*
Skolnick et al (Trends in Biotech, 18(1):34-39, 2000).*
Doerks et al, (TIG 14(6):248-250, 1998).*
Smith et al (Nature Biotechnology, 15:1222-1223, 1997).*
Brenner (TIG, 15(4):132-133, 1999).*
Bork et al (TIG 12(10):425-427, 1996).*
May et al (Biochemistry 42:8250-8259, 2003).*
See Attwood (Science, 290:471-473, 2000).*
Gerhold et al. (BioEssay, 18(12):973-981, 1996).*
Wells et al. (Journal of Leukocyte Biology, 61(5):545-550, 1997).*
Russell et al. (Journal of Molecular Biology, 244:332-350, 1994).*
http://www.medterms.com.*
Beers, "The Merk Manual of Diagnosis and Therapy, Seventeenth Edition" pp. 556-568, 1044-1050 and 1110-1113 (1999).
Falk et al., "Expression of a human α-1,3/4-Fucosyltransferase in the pit cell linease of FVB/N mouse stomach results in production of $Le^b$—containing glycoconjugates: a potential transgenic mouse model for studying He licobacter pylori infection" *Proc. Natl. Acad. Sci. USA* 92:1515-1519 (1995).
Lemercinier et al., "High-resolution solution structure of human intestinal trefoil factor and functional insights from detailed structural comparisons with the other members of the trefoil family of mammalian cell motility factors" *Biochemistry* 40:9552-9559 (2001).
Podotsky et al., "Latent transformed growth-inhibiting factor in human malignant effusions" *Cancer Res.* 48:418-424 (1988).
Amorim et al., "Microparticles for delivering therapeutic peptides and proteins to the lumen of small intestine," *European J. Pharmaceutics and Biopharmaceutics* 52:39-44 (2001).
Chinery et al., "Combined intestinal trefoil factor and epidermal growth factor is prophylactic against indomethacin-induced gastric damage in the rat," *Clinical Science* 88:401-403 (1995).
McKenzie et al., "Topical and intravenous administration of trefoil factors protect the gastric mucosa from ethanol-induced Injury in the rat," *Aliment Pharmacol. Ther.* 14:1033-1040 (2000).
Poulsen et al., "Metabolism of oral trefoil factor 2 (TFF2) and the effect of oral and parenteral TFF2 on gastric and duodenal ulcer healing in the rat," *Gut* 45:516-522 (1999).
Tebbutt et al., "Reciprocal regulation of gastrointestinal homeostasis by SHP2 and STAT-mediated trefoil gene activation in gp130 mutant mice," *Nature Medicine* 8:1089-1097 (2002).
Wang et al., "Effect of antibody against integrin α4 on bleomycin-induced pulmonary fibrosis in mice," *Biochem. Pharmacol.* 60:1949-1958 (2000).
Wang et al., Inflammation intersection: gp 130 balances gut imitation and stomach cancer, *Nature Medicine* 8:1080-1082 (2002).

Babyalsk et al., "Oral trefoil peptides protect against ethanol- and indomethacin-induced gastric injury in rats" *Gastroenterology* 110:489-497 (1996).
Beck et al., "Growth factors in inflammatory bowel disease" *Inflammatory Bowel Disease* 5(1):44-60 (1999).
Byrne et al., "rHuKGF ameliorates sympoms in DSS and CD4'CD45RB' T cell transfer mouse models of inflammatory bowel disease" *Am. J. Physiol. Gastrointost. Livor Physiol.* 282:G690-G701 (2002).
Dignass et al., "Trefoil peptides promote epithelial migration through a transforming growth factor β-independent pathway" *J. Clin. Invest.* 94:376-383 (1994).
Frandsen et al, "Receptor binding of pancreatic spasmolytic polypeptide (PSP) in rat intestinal mucosal cell membranes inhibits the adenylate cyclase activity" *Regulatory Peptides* 16:291-297 (1986).
Hauser et al., "hP1.B. a human P-domain peptide homologous with rat intestinal trefoil factor, is expressed also in the ulcer-associated cell lineage and the uterus" *Proc Natl. Acad. Sci. USA* 90:6961-6965 (1993).
Itoh et al., "A paradoxial reduction in susceptibility to colonic injury upon targeted transgenic ablation of goblet cells" *The Journal of Clinical Investigation* 104(11):1539-1547 (1999).
Itoh et al., "Goblet-cell-specific transcription of mouse intestinal trefoil factor gene results from collaboration of complex series of positive and negative regulatory elements" *Biochom. J.* 341:461-472 (1999).
Iwakiri et al., "A silencer inhibitor confers specific expression of intestinal trefoil factor in gobletlike cell lines" *Am. J. Physiol. Gastrointest. Liver Physiol.* 208 G1114-G1123 (2001).
Iwakiri et al., "Keratinocyte growth factor promotes goblet cell differentiation through regulation of goblet cell silencer inhibitor" *Gastroenterology* 120:1372-1380 (2001).
Jakowlew et al., "Sequence of the pS2 mRNA induced by estrogen in the human breast cancer cell line MCF-7" *Nucleic Acis Res.* 12:2861-2878 (1984).
Jeffrey et al., "Spasmolytic polypeptide: A trefoil peptide secreted by rat gastic mucous cells" *Gastroenterology* 106:336-345 (1994).
Jorgensen et al, "Pancreatic spasmolytic polypeptide (PSP): I. Preparation and initial chemical characterization of a new polypeptide from porcine pancreas" *Regulatory Peptides* 3:207-219 (1982).
Jorgensen et al, "Pancreatic spasmolytic polypeptide (PSP): III Pharmacology of a new porcine pancreatic polypeptide with spasmolytic and gastric acid secretion inhibitory effects" *Regulatory Peptides* 3:231-243 (1982).
Kanai et al., "Intestinal trefoil factor induces inactivation of extracellular signal-regulated protein kinase in intestinal epithelial cells" *Proc. Natl. Acad. Sci. USA* 95:178-182 (1998).
Kannan et al., "Human pS2/trefoil factor 1: production and characterization in *pichia pastoris*" *Protein Expression and Purification* 21:92-98 (2001).
Kato et al., "Effects of growth factors and trefoil peptides on migration and replication in primary oxyntic cultures" *Am J. Physiol.* 276 (*Gastrointest. Liver Physiol.* 39): G1105-G1116 (1999).
Kindon et al., "Trefoil peptide protection of intestinal epithelial barrier function: cooperative interaction with mucin glycoprotein" *Gastroenterology* 109:516-523 (1995).
Kinoshita et al., "Distinct pathways of cell migration and antiapoptotic response to epithelial injury: structure-function analysis of human intestinal trefoil factor" *Molecular and Cellular Biology* 20(13):4680-4690 (2000).
Mashimo et al. "Impaired defense of intestinal mucosa in mice lacking intestinal trefoil factor" *Science* 274:262-265 (1996).
Modlin et al., "Trefoil Peptides: Mitogens. Motogens. or Mirages?" *J. Clin. Gastroenterol* 25(Suppl. 1):S94-S100 (1997).
Ogata et al., "Identification of a goblet-cell-specific enhancer element in the rat intestinal trefoil factor gene promoter bound by a goblet cell nuclear protein" *The Journal of Biological Chemistry* 273(5):3060-3067 (1998).
Ogata et al., "Trefoil peptide expression and secretion is regulated by neuropeptides and acetylcholine" *Am. J. Physiol.* 273 (*Gastrointest. Liver Physiol* 36):G348-G354 (1997).

Playford, "Trefoil peptides: what are they and what do they do?" *Journal of the Royal College of Physicians of London* 31(1):37-41 (1997).
Podolsky et al., "Human colonic goblet cells—demonstration of distinct subpopulations defined by mucin-specific monoclonal antibodies" *J. Clin. Invest.* 77:1263-1271 (1986).
Podolsky et al., "Identification of human intestinal trefoil factor" *Journal of Biological Chemistry* 268:6694-6702 (1993).
Rio et al., "Breast cancer-associated pS2 protein: Synthesis and secretion by normal stomach mucosa" *Science* 241:705-708 (1988).
Sands et al., "The trefoil peptide family" *Annual Review of Physiology* 58:253-273 (1996).
Sands et al., "Molecular cloning of the rat intestinal trefoil factor gene" *The Journal of Biological Chemistry* 270(16):9353-9361 (1995).
Suemori et al., "Identification and characterization of rat intestinal trefoil factor: Tissue- and cell-specific member of the trefoil protein family" *Proc. Natl. Acad. Science USA* 88:11017-11021 (1991).
Taupin et al., "Intestinal trefoil factor confers colonic epithelial resistance to apoptosis" *Proc. Nat. Acad. Sci.* 97(2):799-804 (2000).
Taupin et al., "Mitogen-activated protein kinase activation regulates intestinal epithelial differentiation" *Gastroenterology* 116:1072-1080 (1999).
Thim et al., "Pancreatic spasmolytic polypeptide (PSP): II. Radioimmunological determination of PSP in porcine tissues, plasma and pancreatic juice" *Regulatory Peptides* 3:221-230 (1982).
Thim et al., "Characterization of human and rat intestinal trefoil factor produced in yeast" *Biochemistry* 34:4757-4764 (1995).
Thim et al., "The amino acid sequence of pancreatic spasmolytic polypeptide" *Biochem. Biophys. Acta.* 827:410-418. (1985).
Tran et al., "Trefoil peptide TFF2 (spasmolytic polypeptide) potently accelerates healing and reduces inflammation in a rat model of colitis" Gut. 44:636-642 (1999).
Xian et al., "Temporal changes in TFF3 expression and jejunal morphology during methotrexate-induced damage and repair," *Am. J. Physiol.* 277 (*Gastrointest. Liver Physiol*. 40): G785-G795 (1999).
Communication and Supplementary European Search Report mailed Apr. 4, 2005 (EP 02 75 7620).
U.S. Appl. No. 07/655,965, filed Feb. 14, 1991, Podolsky.
U.S. Appl. No. 07/837,192, filed Feb. 13, 1992, Podolsky.
U.S. Appl. No. 10/362,310, filed Feb. 19, 2003, Podolsky.
U.S. Appl. No. 10/457,157, filed Jun. 9, 2003, Podolsky.
Alderman et al., "Insights into the mechanisms of gastric adaptation to aspirin-induced injury: A role for regenerating protein but not trefoil peptides," *Lab Invest.* 83:1415-1425 (2003).
Bare et al., "Effect of cysteine substitutions on the mitogenic activity and stability of recombinant human keratinocyte growth factor," *Biochem Biophys Res Commun.* 205(1):872-879 (1994).
Botoman et al., "Management of inflammatory bowel disease," *Am Fam Physician.* 57:57-68 (1998).
Burling et al., "Effect of topical administration of epidermal growth factor on healing of corneal epithelial defects in horses," *Am J Vet Res.* 61:1150-55 (2000).
Cook et al., "Oral human spasmolytic polypeptide protects against aspirin-induced gastric injury in rats," *J Gastroenterol Hepatol.* 13:363-370 (1998).
Fleiszig et al., "Relationship between cytotoxicity and corneal epithelial cell invasion by clinical isolates of *Pseudomonas aeruginosa*," *Infect Immun.* 64(6): 2288-2294 (1996).
Hammer, "Was gibt es neues in der diagnostik und therapie des morbus crohn und der colitis ulcerosa," *Schweiz. Med. Wochenschr.* 124:452-460 (1994). (Abstract in English).
Hanby et al., "Expression of the trefoil peptides pS2 and human spasmolytic polypeptide (hsp) in barrett's metaplasia and the native oesophageal epithelium: delineation of epithelial phenotype," *J of Pathol.* 173:213-219 (1994).
Harlow et al., "Antibodies: A Laboratory Manual," Cold Spring Harbor Press Inc. 72-73 (1988).
Harmer et al., "The crystal structure of fibroblast growth factor (FGF) 19 reveals novel features of the FGF family and offers a structural basis for its unusual receptor affinity," *Biochemistry* 43(3): 629-640 (2004).

Hawkey et al., "Gastrointestinal safety of AZD3582, a cyclooxygenase inhibiting nitric oxide donator: proof of concept study in humans," *Gut* 52:1537-1542 (2003).
http://allaboutvision.com/conditions/cataracts.htm.
http://allaboutvision.com/conditions/diabetic.htm.
http://allaboutvision.com/conditions/dryeye.htm.
http://allaboutvision.com/conditions/glaucoma.htm.
http://allaboutvision.com/conditions/hyperopia.htm.
http://allaboutvision.com/conditions/amd.htm.
http://medterms.com; definition of mucositis.
http://www.mic.ki.se/Diseases/C11.html.
http://www.hon.ch; definition of gastrointestinal system.
http://www.medterms.com; definition of gastrointestinal tract.
http://www.cancerweb.ncl.ac.uk; definition of gastrointestinal tract.
http://www.cancerweb.ncl.ac.uk; definition of trefoil.
http://www.thedoctorsdoctor.com; definition/description of gastrointestinal tract.
Life Sciences Dictionary; definition of lesion.
Mori et al., "Identification of a polypeptide secreted by human breast cancer cells (MCF-7) as the humam estrogen-responsive gene (pS2) product," *Biochem Biophys Res Comm.* 155:366-372 (1988).
Moss and Wright, "Molecular aspects of mucosal repair: a summary," *Yale Journal of Biology and Medicine* 69(2): 155-158 (1996).
MSN Encarta Dictionary; definition for trefoil.
MSN Encarta dictionary definitions of homologous and homologue.
Muskett et al., "Solution structure of the disulfide-linked dimer of human intestinal trefoil factor (TFF3): The intermolecular orientation and interactions are markedly different from those of other dimeric trefoil proteins," *Biochemistry* 42:15139-15147 (2003).
Ngo et al., "Computational complexity, protein structure prediction, and the Levinthal paradox," *The Protein Folding Problem and Tertiary Structure Prediction* K. Merz and S. Le Grand, Editors 491-495 (1994).
Nikolaidis et al., "Trefoil factor-2 is an allergen-induced gene regulated by Th2 cytokines and STAT6 in the lung," *Am J Resp Cell Mol Biol.* 29:458-464 (2003).
Okayasu et al., "A novel method in the induction of reliable experimental acute and chronic ulcerative colitis in mice," *Gastroenterology* 98:694-702 (1990).
On-Line Medical Dictionary; definition of cervix uteri-synonym is cervix.
On-Line Medical Dictionary; definition of mucositis.
Pharyngula; http://pharygula.org/index/weblog/comments/evolution_of_the_mammalian_vagina.
Paulsen et al., "TFF peptides in the human efferent tear ducts," *Invest Ophthalmol Vis Sci.* 43:3359-3364 (2002).
Poulsen et al., "Injected TFF1 and TFF3 bind to TFF2-immunoreactive cells in the gastrointestinal tract in rats," *Reg Peptides* 115:91-99 (2003).
Poulsom et al., "Trefoil peptides: a newly recognized family of epithelial mucin-associated molecules," *Am J Physiol.* 265:G205-213 (1993).
Richter et al., "Contribution of the transforming growth factor alpha B-loop beta-sheet to binding and activation of the epidermal growth factor receptor," *J Biol Chem.* 270(4): 1612-1616 (1995).
Segars et al., "Mesalamine and olsalazine:5-aminosalicylic acid agents for the treatment of inflammatory bowel disease," *Clin Pharm.* 11:514-528 (1992).
Silva et al., "Trefoil factor family domain peptides in the human respiratory tract," *J Pathol* 190:133-142 (2000).
Smith et al., "Production of human beta interferon in insect cells infected with a baculovirus expression vector," *Molecular and Cellular Biology* 3(12):2156-2165 (1983).
Stein et al., "Comparative tolerability of treatments for inflammatory bowel disease," *Drug Saf.* 23:429-448 (2000).
Tesfaigzi, "Processes involved in the repair of injured airway epithelia," *Arch Immunol Ther Exp.* 51:283-288 (2003).
Thim, "Trefoil peptides: A new family of gastrointestinal molecules," *Digestion* 55:353-360 (1994).
Tomasetto et al., "hSp, the domain-duplicated homolog of pS2 protein, is co-expressed with the pS2 in stomach but not in breast carcinoma," *The EMBO Journal* 9(2): 407-414 (1990).

Van de Bovenkamp et al, "Gastric-type mucin and TFF-peptide expression in Barrett's oesophagus is disturbed during increased expression of MUC2," *Histopathology* 42:555-565 (2003).
Williams et al., "pS2 transfection of murine adenocarcinoma cell line 410.4 enhances dispersed growth pattern in a 3-D collagen gel," *J Cell Sci.* 109:63-71 (1996).
Yoo et al., "Cytokines In restitution; gastrointestinal mucosal repair and experimental therapeutics," Front. Gastrointest. Res. Basel, Karger 25:14-28 (2002).
Zhang, "The therapeutic effect of recombinant human trefoil factor 3 on hypoxia-induced necrotizing enterocolitis in Immature rat," *Regul Pept.* 116:53-60 (2003).
International Search Report mailed Aug. 31, 2006 (PCT/US03/34796).
Alderman et al., "Insights into the mechanisms of gastric adaptation to aspirin-induced injury: A role for regenerating protein but not trefoil peptides," *Laboratory Investigation* 83:1415-1425 (2003).
Babyatsky et al., "Trefoil peptides protect against ethanol and indomethacin induced gastric injury in rats," *Gastroenterology* 106:A43 (1994).
Hanby et al., "Expression of the trefoil peptides pS2 and human spasmolytic polypeptide (hsp) in barrett's metaplasia and the native oesophageal epithelium: delineation of epithelial phenotype," *J. of Pathology* 173:213-219 (1994).
Hawkey et al., "Gastrointestinal safety of AZD3582, a cyclooxygenase inhibiting nitric oxide donator: proof of concept study in humans," *Gut* 52:1537-1542 (2003).
Muskett et al., "Solution structure of the disulfide-linked dimer of human intestinal trefoil factor (TFF3): The intermolecular orientation and interactions are markedly different from those of other dimeric trefoil proteins," *Biochemistry* 42:15139-15147 (2003).
Poulsom et al., "Trefoil peptides: a newly recognized family of epithelial mucin-associated molecules," *Am. J. Physiol.* 265:G205-213 (1993).
Thim, "Trefoil peptides: A new family of gastrointestinal molecules," Digestion 55:353-360 (1994).
Van de Bovenkamp et al, "Gastric-type mucin and TFF-peptide expression in Barrett's oesophagus is distrubed during increased expression of MUC2," *Histopathology* 42:555-565 (2003).
Williams et al., "pS2 transfection of murine adenocarcinoma cell line 410.4 enhances dispersed growth pattern in a 3-D collagen gel," *J. Cell Sci.* 109:63-71 (1996).
Zhang, "The therapeutic effect of recombinant human trefoil factor 3 on hypoxia-induced necrotizing enterocolitis in immature rat," *Regulatory Peptides* 116:53-60 (2003).
U.S. Appl. No. 11/821,367, filed Jun. 21, 2007, Podolsky.
Blast alignment of human and rat ITF, currently known as trefoil factor 3 (TTF3).
Communication and Search Results from European Patent Office, mailed May 16, 2006 (EP 97921148.9).
Cuzzocrea et al., "Celecoxib, a selective cyclo-oxygenase-2 inhibitor reduces the severity of experimental colitis induced by dinitrobenzene sulfonic acid in rats," *Eur. J. Pharmacol.* 431:91-102 (2001).
David et al., "Corneal wound healing modulation using basic fibroblast growth factor after excimer laser photorefractive keratectomy," *Cornea* 14:227-234 (1995).
Dorland's Medical Dictionary; definition of mucositis.
Göke et al., "Trefoil peptides promote restitution of wounded corneal epithelial cells," *Exp. Cell Res.* 264:337-344 (2001).
Harlow and Lane, "Antibodies: a laboratory manual," *Cold Spring Harbor Press Inc.*, p. 76 (1988).
Hauser et al., "xP2, a New Member of the P-Domain Family of Potential Growth Factor Members, is Synthesized in *Xenopus laevis* Skin," *J. Biol. Chem.* 267(20):14451-14455 (1992).
Jagla et al., "Localization of TFF3 peptide to porcine conjunctival goblet cells," *Cell Tissue Res.* 296:525-530 (1999).
Juhász et al., "Repopulation of langerhans cells during wound healing in an experimental human skin/SCID mouse model," *Immunol. Lett.* 52:125-128 (1996).
Kalin and Bjorkholm, "Prophylactic and empirical treatment of mycoses in neutropenic fever," *Lakartidningen* 98(16):1899-1903 (2001), abstract only.

Khan-Lim et al., "Trefoil factors in normal and dry eyes," *Trefoils & Mucins 2002*, Keble College, Oxford, U.K., Apr. 2-4, 2002 (abstract).
Mason, "Functional analysis of the cysteine residues of activin A," *Mol. Endocrinol.* 8(3):325-332 (1994).
Medical Encyclopedia: Uveitis from http://www.nlm.nih.gov/medlineplus/print/ency/article/001005.htm.
Murali et al., "Effect of topically administered platelet-derived growth factor on corneal wound strength," *Curr. Eye Res.* 13:857-862 (1994).
National Cancer Institute: Dictionary of Cancer Terms; definition of lesion.
Paulsen et al., "Distribution of TFF-peptides and mucins in human nasolacrimal ducts," *Trefoils & Mucins 2002*, Keble College, Oxford, U.K., Apr. 2-4, 2002 (abstract).
Paulsen et al., "Distribution of mucins in human pterygia," *Trefoils & Mucins 2002*, Keble College, Oxford, U.K., Apr. 2-4, 2002 (abstract).
Poulsen et al., "Luminal and parental TFF2 and TFF3 dimer and monomer in two models of experimental colitis in the rat," *Regulatory Peptides* 126:163-171 (2005).
Taupin and Podolsky, "Mitogen-activated protein kinase activation regulates intestinal epithelial differentiaiton," *Gastroenterology* 116:1072-1080 (1999).
Websters Dictionary—definition trefoil.
Office Action for U.S. Application No. 10/266,069 (mailed Feb. 27, 2007).
Office Action for U.S. Application No. 10/434,636 (mailed Sep. 30, 2004).
Office Action for U.S. Appl. No. 10/434,636 (mailed Feb. 14, 2006).
Office Action for U.S. Appl. No. 10/434,636 (mailed Jun. 1, 2007).
Office Action for U.S. Appl. No. 10/235,238 (mailed Feb. 27, 2006).
Office Action for U.S. Appl. No. 10/235,238 (mailed Nov. 27, 2006).
Office Action for U.S. Appl. No. 10/435,406 (mailed Oct. 7, 2004).
Office Action for U.S. Appl. No. 10/435,406 (mailed Feb. 13, 2006).
Office Action for U.S. Appl. No. 10/435,406 (mailed Jun. 4, 2007).
Office Action for U.S. Appl. No. 10/434,607 (mailed Sep. 30, 2004).
Office Action for U.S. Appl. No. 10/434,607 (mailed Feb. 15, 2006).
Office Action for U.S. Appl. No. 10/434,607 (mailed Jun. 1, 2007).
Office Action for U.S. Appl. No. 10/305,747 (mailed Nov. 4, 2005).
Office Action for U.S. Appl. No. 10/305,747 (mailed May 23, 2006).
Office Action for U.S. Appl. No. 10/431,805 (mailed Sep. 30, 2004).
Office Action for U.S. Appl. No. 10/431,805 (mailed Dec. 20, 2005).
Office Action for U.S. Appl. No. 10/431,805 (mailed Jun. 1, 2007).
Office Action for U.S. Appl. No. 10/397,953 (mailed Sep. 30, 2004).
Office Action for U.S. Appl. No. 10/397,953 (mailed Feb. 15, 2006).
Office Action for U.S. Appl. No. 10/397,953 (mailed Nov. 2, 2007).
Office Action for U.S. Appl. No. 10/698,572 (mailed Jun. 15, 2007).
Office Action for U.S. Appl. No. 07/655,965 (mailed Feb. 24, 1992).
Office Action for U.S. Appl. No. 08/191,352 (mailed Sep. 2, 1994).
Office Action for U.S. Appl. No. 08/191,352 (mailed Apr. 4, 1995).
Office Action for U.S. Appl. No. 08/191,352 (mailed Dec. 22, 1995).
Office Action for U.S. Appl. No. 08/191,352 (mailed Sep. 9, 1996).
Office Action for U.S. Appl. No. 08/191,352 (mailed Apr. 30, 1997).
Office Action for U.A. Patent No. 6,063,755 (mailed Sep. 9, 1996).
Office Action for U.A. Patent No. 6,063,755 (mailed Jun. 11, 1997).
Office Action for U.A. Patent No. 6,063,755 (mailed Aug. 19, 1998).
Office Action for U.A. Patent No. 6,063,755 (mailed May 24, 1999).
Office Action for U.A. Patent No. 6,316,218 (mailed Jan. 22, 1999).
Office Action for U.A. Patent No. 6,221,840 (mailed Apr. 2, 1997).
Office Action for U.A. Patent No. 6,221,840 (mailed Jan. 6, 1998).
Office Action for U.A. Patent No. 6,221,840 (mailed Apr. 2, 1999).
Office Action for U.A. Patent No. 6,221,840 (mailed Dec. 27, 1999).
Office Action for U.A. Patent No. 6,221,840 (mailed Jul. 10, 2000).
Office Action for U.S. Appl. No. 10/353,334 (mailed Feb. 8, 2007).
Office Action for U.S. Appl. No. 10/353,334 (mailed Oct. 22, 2007).
Office Action for U.S. Appl. No. 10/362,310 (mailed Feb. 12, 2007).
Office Action for U.A. Patent No. 6,426,404 (mailed Jan. 20, 2000).
Office Action for U.A. Patent No. 6,426,404 (mailed Oct. 24, 2000).
Office Action for U.A. Patent No. 6,426,404 (mailed Jul. 17, 2001).
Office Action for U.A. Patent No. 6,525,018 (mailed Jul. 3, 2001).
Office Action for U.A. Patent No. 6,525,018 (mailed Jun. 25, 2002).
Office Action for U.S. Appl. No. 10/313,642 (mailed Mar. 16, 2004).
Office Action for U.S. Appl. No. 10/313,642 (mailed Dec. 22, 2004).
Office Action for U.S. Appl. No. 10/313,642 (mailed Feb. 15, 2006).

Office Action for U.S. Appl. No. 10/313,642 (mailed Nov. 15, 2006).
Office Action for U.S. Appl. No. 10/449,456 (mailed Oct. 1, 2004).
Office Action for U.S. Appl. No. 10/449,456 (mailed Feb. 15, 2006).
Office Action for U.S. Appl. No. 10/449,456 (mailed Jun. 15, 2007).
Office Action for U.S. Appl. No. 10/457,157 (mailed Mar. 16, 2004).
Office Action for U.S. Appl. No. 10/457,157 (mailed Apr. 13, 2005).
Office Action for U.S. Appl. No. 10/457,157 (mailed May 25, 2006).
Office Action for U.S. Appl. No. 10/457,157 (mailed Feb. 20, 2007).
Amorim et al., "Microparticles for delivering therapeutic peptides and proteing to the lumen of small intestine," *European J. Pharmaceutics and Biopharmaceutics* 52:39-44 (2001).
Babyatsky et al., "Trefoil peptides protect against ethanol and indomethacin induced gastric injury in rats," *Gastroenterology* 106:A43 (1994).
Babyatsky et al., "Oral trefoil peptides protect against ethanol- and indomethacin-induced gastric injury in rats" *Gastroenterology* 110:489-497 (1996).
Beers, "The Merk Manual of Diagnosis and Therapy, Seventeenth Edition" pp. 556-568, 1044-1050 and 1110-1113 (1999).
Chinery et al., "Combined intestinal trefoil factor and epidermal growth factor is prophylactic against indomethacin-induced gastric damage in the rat," *Clinical Science* 88:401-403 (1995).
Graness et al., "Protein kinase C and ERK activation are required for TFF-peptide-stimulated bronchial epithelial cell migration and tumor necrosis factor-alpha-induced interleukin-6 (IL-6) and IL-8 secretion," *J. Biol. Chem.* 277:18440-18446 (2002).
Hauser et al., "hP1.B, a human P-domain peptide homologous with rat intestinal trefoil factor, is expressed also in the ulcer-associated cell lineage and the uterus" *Proc. Natl. Acad. Sci. USA* 90:6961-6965 (1993).
Hoffman et all., "Molecular medicine of TFF-peptides: From gut to brain," *Histo. and Histopathol.* 16:319-334 (2001).
Kindon et al., "Trefoil peptide protection of intestinal epithelial barrier function: cooperative interaction with mucin glycoprotein" *Gastroenterology* 109:516-523 (1995).
Kjellev et al., "Effect of systemically administered TFF3 on murine experimental colitis," *IV TFF Conference*, Strasbourg, France (Abstract/Poster) (Dec. 2-4, 2004).
Lefebvre et al., "The mouse one P-Domain (pS2) and two P-Domain (*m*SP) genes exhibit distinct patterns of expression," *J. Cell Biol.* 122:191-198 (1993).
Mashimo et al. "Impaired defense of intestinal mucosa in mice lacking intestinal trefoil factor" *Science* 274:262-265 (1996).
McKenzie et al., "Topical and intravenous administration of trefoil factors protect the gastric mucosa from ethanol-induced injury in the rat," *Aliment Pharmacol. Ther.* 14:1033-1040 (2000).
Modlin et al., "Trefoil Peptides: Mitogens, Motogenes, or Mirages?" *J. Clin. Gastroenterol.* 25(Suppl. 1):S94-S100 (1997).
Oertel et al., "Trefoil factor family—peptides promote migration of human bronchial epithelial cells" *Am. J. Respir. Cell Mol. Biol.* 25:418-424 (2001).
Podolsky et al., "Identification of human intestinal trefoil factor," *J. Biol. Chem.* 268:6694-6702 (1993).

Poulsen et al., "Metabolism of oral trefoil factor 2 (TFF2) and the effect of oral and parenteral TFF2 on gastric and duodenal ulcer healing in the rat," *Gut* 45:516-522 (1999).
Tran et al., "Trefoil peptide TFF2 (spasmolytic polypeptide) potently accelerates healing and reduces inflammation in a rat model of colitis" *Gut.* 44:636-642 (1999).
Wang et al., "Effect of antibody against integrin α4 on bleomycin-induced pulmonary fibrosis in mice," *Biochem. Pharmacol.* 60:1949-1958 (2000).
Wiede et al., "Synthesis and localization of the mucin-associated TFF-peptides in the human uterus," *Cell Tissue Res.* 303:109-115 (2001).
International Search Report mailed Jul. 24, 1997 (PCT/US97/06004).
International Search Report mailed Sep. 11, 2002 (PCT/US02/12891).
International Search Report mailed Mar. 28, 2003 (PCT/US02/31998).
International Search Report mailed May 27, 2003 (PCT/US02/38258).
International Search Report mailed Oct. 20, 2003 (PCT/US03/09195).
Communication and Supplementary European Search Report mailed Jun. 1, 2004 (EP 02 76 4324).
Communication and Supplementary European Search Report mailed Jul. 5, 2004 (EP 97 92 1148).
International Search Report mailed Oct. 8, 2004 (PCT/US02/28339).
Communication and Supplementary European Search Report mailed Jan. 25, 2005 (EP 02 78 6828).
Communication and Supplementary European Search Report mailed Apr. 4, 2005 (EP 02 75 7620).
Communication and Supplementary European Search Report mailed Apr. 15, 2005 (EP 02 80 0937).
Beck et al., "Chemotherapy- and radiotherapy-induced intestinal damage is regulated by intestinal trefoil factor," *Gastroenterology* 126:796-808 (2004).
Office Action for U.S. Appl. No. 11/275,600 (mailed Apr. 2, 2008).
Office Action for U.S. Appl. No. 10/266,069 (mailed May 20, 2008).
Office Action for U.S. Appl. No. 10/434,636 (mailed Mar. 14, 2008).
Office Action for U.S. Appl. No. 10/435,406 (mailed May 14, 2008).
Office Action for U.S. Appl. No. 10/434,607 (mailed Mar. 26, 2008).
Office Action for U.S. Appl. No. 10/431,805 (mailed Mar. 20, 2008).
Office Action for U.S. Appl. No. 10/397,953 (mailed Mar. 20, 2008).
Office Action for U.S. Appl. No. 11/275,599 (mailed Apr. 2, 2008).
Office Action for U.S. Appl. No. 10/353,334 (mailed Jul. 30, 2008).
Office Action for U.S. Appl. No. 10/362,310 (mailed May 15, 2008).
Office Action for U.S. Appl. No. 10/313,642 (mailed Apr. 8, 2008).
Office Action for U.S. Appl. No. 10/449,456 (mailed Apr. 1, 2008).
Office Action for U.S. Appl. No. 10/457,157 (mailed Jul. 2, 2008).
Declaration under 37 C.F.R. § 1.132 for U.S. Appl. No. 09/056,868 (executed Jun. 12, 1998).
Sequence alignment from European Patent Application No. 97921148.9 (submitted to European Patent Office on Aug. 7, 2006).

\* cited by examiner

FIGURE 1A

```
1    MLGLVLALLS  SSSAEEYVGL  SANQCAVPAK  DRVDCGYPHV
41   TPKECNNRGC  CFDSRIPGVP  WCFKPLQEAE  CTF          (SEQ ID NO.:1)
```

FIGURE 1B

```
1    atgctggggc  tggtcctggc  cttgctgtcc  tccagctctg  ctgaggagta  cgtgggcctg
61   tctgcaaacc  agtgtgccgt  gccagccaag  gacagggtgg  actgcggcta  cccccatgtc
121  acccccaagg  agtgcaacaa  ccggggctgc  tgctttgact  ccaggatccc  tggagtgcct
181  tggtgtttca  agcccctgca  ggaagcagaa  tgcaccttct  ga          (SEQ ID NO.:2)
```

FIGURE 2A

```
1    MATMENKVIC ALVLVSMLAL GTLAEAQTET CTVAPRERQN
41   CGFPGVTPSQ CANKGCCFDD TVRGVPWCFY PNTIDVPPEE
81   ECEF          (SEQ ID NO.:3)
```

FIGURE 2B

```
1    atggccacca tggagaacaa ggtgatctgc gccctggtcc tggtgtccat gctggccctc
61   ggcaccctgg ccgaggccca gacagagacg tgtacagtgg ccccccgtga agacagaat
121  tgtggttttc ctggtgtcac gccctcccag tgtgcaaata agggctgctg tttcgacgac
181  accgttcgtg gggtccctg gtgcttctat cctaatacca tcgacgtccc tccagaagag
241  gagtgtgaat tttag    (SEQ ID NO.:4)
```

FIGURE 3A

```
1   EKPSPCQCSR  LSPHNRTNCG  FPGITSDQCF  DNGCCFDSSV
41  TGVPWCFHPL  PKQESDQCVM  EVSDRRNCGY  PGISPEECAS
81  RKCCFSNFIF  EVPWCFFPNS  VEDCHY           (SEQ ID NO.:5)
```

FIGURE 3B

```
1    atgggacggc gagacgccca gctcctggca gcgctcctcg tcctggggct atgtgccctg
61   gcggggagtg agaaaccctc ccctgccag  tgctccaggc tgagccccca taacaggacg
121  aactgcggct ccctggaat  caccagtgac cagtgttttg acaatggatg ctgtttcgac
181  tccagtgtca ctggggtccc ctggtgtttc cacccctcc  caaagcaaga gtcggatcag
241  tgcgtcatgg aggtctcaga ccgaagaaac tgtggctacc cgggcatcag ccccgaggaa
301  tgcgcctctc ggaagtgctg cttctccaac ttcatctttg aagtgccctg gtgcttcttc
361  ccgaagtctg tggaagactg ccattactaa      (SEQ ID NO.:6)
```

FIGURE 4

```
TFF1(30-70)     xct-vaprerqncgfpgvtpsqcankgccfddtvrgvpwcfx    SEQ ID NO.:7
TFF2-1(30-71)   xcsrlsphnrtncgfpgitsdqcfdngccfdssvtgvpwcfx    SEQ ID NO.:8
TFF2-2(80-120)  xcv-mevsdrrncgypgispeecasrkccfsnfifevpwcfx    SEQ ID NO.:9
TFF3(24-64)     xca-vpakdrvdcgyphvtpkecnnrgccfdsripgvpwcfx    SEQ ID NO.:10
```

METHODS AND COMPOSITIONS FOR TREATING ORAL AND ESOPHAGEAL LESIONS

CROSS REFERENCE TO RELATED APPLICATIONS

This application is a continuation-in-part of U.S. application Ser. No. 10/131,063, filed Apr. 24, 2002 now abandoned, which claims the benefit of U.S. Provisional Application No. 60/286,240, filed Apr. 24, 2001.

This application also claims the benefit of U.S. Provisional Application No. 60/422,708, filed Oct. 31, 2002.

FIELD OF THE INVENTION

This invention provides methods and compositions for treating lesions of the upper alimentary canal including the oral cavity and esophagus.

BACKGROUND OF THE INVENTION

Oral mucositis is the destruction of the oral mucosal epithelium which results in erythema, ulcerations, and pain in the oral cavity. Mucositis often arises as a complication of antineoplastic therapy such as cancer chemotherapy or radiotherapy. The painful ulcerative lesions of mucositis can cause patients to restrict their oral intake of food and liquids; as a result, they lose weight and suffer from dehydration. Severe mucositis can necessitate the de-escalation or the complete interruption of anti-neoplastic therapy. Chemotherapy or radiotherapy can also disrupt mucosal epithelium more distally in the gastrointestinal tract including the esophagus, stomach, and small and large intestines, resulting in pain and organ dysfunction (i.e., diarrhea).

The mucositis lesions are also sites of secondary infections, acting as portals of entry for endogenous oral microorganisms; a particularly serious concern in patients who are immunocompromised. Mucositis is therefore a significant risk factor for chronic debilitating local infections (e.g. yeast (Candida) infections) as well as life-threatening systemic infection (septicemia). Patients with mucositis and neutropenia have a relative risk of septicemia that is at least four times greater than that of individuals without mucositis.

Aphthous ulcers of the mouth (or aphthous stomatitis) are a common and painful problem; approximately 10% of the population suffers from these mouth sores at one time or another. The cause of outbreaks of aphthous sores are not well understood, although they tend to be associated with stress and minor injury to the inside of the mouth. No satisfactory treatments are available, although topical application of steroids provides relief for some patients.

SUMMARY OF THE INVENTION

This invention features a method for treating a lesion of the upper alimentary canal in a mammal by administering to the mammal a therapeutically effect amount of a trefoil peptide. Preferably, the mammal is a human. Treatment or prevention of lesions according to the invention can speed healing, reduce pain, delay or prevent occurrence of the lesion, and inhibit expansion, secondary infection, or other complications of the lesion. Preferably, the mammal is a human. In particularly useful embodiments, the trefoil peptide is SP, pS2, ITF, $ITF_{15-73}$, $ITF_{21-73}$, $ITF_{1-72}$, $ITF_{15-72}$, or $ITF_{21-72}$, and is present in a pharmaceutical composition containing a pharmaceutically acceptable carrier. Other useful trefoil peptides include polypeptides that are substantially identical to SP, pS2, ITF, $ITF_{15-73}$, $ITF_{21-73}$, $ITF_{15-72}$, or $ITF_{21-72}$. The trefoil peptide may be administered as a monomer, a dimer, or another multimeric form.

Lesions of the upper alimentary canal such as mucositis, aphthous stomatitis, and gingivitis can be treated by the methods of this invention. Additionally, lesions of the upper alimentary canal that result from antineoplastic therapy (i.e., chemotherapy or radiotherapy), Behcet's Disease, biopsy, surgery, tumor resection, thermal or chemical burns, tooth extraction, trauma from any cause, or lesions caused by microbial (i.e., bacterial, viral, or fungal) infection are also amenable to treatment.

In preferred embodiments, the patient is also administered a second therapeutic agent. Preferred second therapeutic agents include anti-inflammatory agents, antibacterial agents (i.e., penicillins, cephalosporins, tetracyclines, or aminoglycosides), antifungal agents (i.e., nystatin or amphotericin B), antiviral agents (i.e., acyclovir), topical antiseptics (i.e., povidone-iodine), analgesics (i.e., lidocaine or benzocaine), or steroids (i.e., triamcinolone or hydrocortisone). Preferably, the second therapeutic agent is administered within 3 days, 1 day, 12 hours, 1 hour, or simultaneously with the trefoil peptide. The second therapeutic agent can be present in the same pharmaceutical composition as the trefoil peptide.

The invention also features pharmaceutical compositions suitable for delivering a trefoil peptide to the upper alimentary canal. Preferably, the pharmaceutical composition is an oral spray, an oral rinse (mouthwash), an ointment, a paste, a cream, a gel, chewing gum, a chewable tablet, a lozenge, or a bioerodable film. In one embodiment, the pharmaceutical compositions use bioerodable microspheres to encapsulate one or more of the therapeutic agents. In preferred embodiments of an oral spray, rinse, ointment, paste, gel, or bioerodable film, a mucoadhesive or viscosity-enhancing agent is present.

In preferred embodiments, the pharmaceutical composition further contains a second therapeutic. Preferred second therapeutic agents include anti-inflammatory agents, antibacterial agents (i.e., penicillins, cephalosporins, tetracyclines, or aminoglycosides), antifungal agents (i.e., nystatin or amphotericin B), antiviral agents (i.e., acyclovir), topical antiseptics (i.e., povidone-iodine), analgesics (i.e., lidocaine or benzocaine), or steroids (i.e., triamcinolone or hydrocortisone).

By "trefoil domain" is meant a polypeptide having a sequence substantially identical to any one of SEQ ID NOs: 7-10, which correspond to the trefoil domains of $hPS2_{30-70}$, $hSP1_{30-71}$, $hSP2_{80-120}$, and $hITF_{24-64}$, respectively, and retain at least one biologic activity characteristic of trefoil peptides. The aligned polypeptide sequences of the four identified human trefoil domains are shown in FIG. 4. It is recognized in the art that one function of the six conserved cysteine residues is to impart the characteristic three-loop (trefoil) structure to the protein. The loop structure conforms to the general intrachain disulfide configuration of $cys_1$-$cyS_5$ (corresponding to amino acid residues 25 and 51 of hITF; SEQ ID NO.:1), $cys_2$-$cys_4$ (corresponding to amino acid residues 35 and 50 of hITF; SEQ ID NO.:1), and $cys_3$-$cys_6$ (corresponding to amino acid residues 45 and 62 of hITF; SEQ ID NO.:1).

By "trefoil peptide (TP)" is meant any polypeptide having at least a trefoil domain (TD) and retaining a biological activity characteristic of trefoil peptides. Thus, preferred TPs may be any mammalian homolog or artificial polypeptide that are substantially identical to human spasmolytic polypeptide (hSP; also known as TFF2, GenBank Accession No. NM_005423; SEQ ID NO.:5), human pS2 (also known as TFF1, GenBank Accession No. XM_009779; SEQ ID NO.: 3), human intestinal trefoil factor (hITF; also known as TFF3, SEQ ID NO.:1), and biologically active fragments of hSP, human pS2, and hITF. If desired, the TP may contain a cysteine residue outside of the trefoil domain suitable for disulfide bonding in the formation of homo- and heterodimers. Most preferably, the additional cysteine is C-terminal to the trefoil domain. Exemplary TPs include $ITF_{1-73}$, $ITF_{15-73}$, $ITF_{21-73}$, $ITF_{15-72}$, $ITF_{21-72}$, $ITF_{1-62}$, $ITF_{1-70}$, $ITF_{1-72}$, and $ITF_{25-73}$. Preferably, a TP is encoded by a nucleic acid molecule that hybridizes under high stringency conditions to the coding sequence of hITF (SEQ ID NO.: 2), hSP (SEQ ID NO.:6), or hpS2 (SEQ ID NO.:4). TPs amenable to methods of this invention may exist as monomers, dimers, or multimers. For example, TP monomers may form an interchain disulfide linkage to form a dimer.

Mammalian trefoil peptides were discovered in 1982. One of the mammalian trefoil peptides, human intestinal trefoil factor (hITF; TFF3), has been characterized extensively, and is described in U.S. Pat. Nos. 6,063,755, and 6,221,840, hereby incorporated by reference. The other two known trefoil peptides are spasmolytic polypeptide (SP; TFF2) and pS2 (TFF1). Intestinal trefoil peptides, described extensively in the literature (e.g., Sands et al., Ann. Rev. Physiol. 58: 253-273, 1996), are expressed in the gastrointestinal tract and have a three-loop structure formed by intrachain disulfide bonds between conserved cysteine residues. These peptides protect the intestinal tract from injury and can be used to treat intestinal tract disorders such as peptic ulcers and inflammatory bowel disease. Homologs of these human polypeptides have been found in a number of non-human animal species. All members of this protein family, both human and non-human, are referred to herein as trefoil peptides. Human ITF will be referred to most extensively in this application; however, the activity of human ITF is common to each of the mammalian trefoil peptides.

By "co-formulated" is meant any single pharmaceutical composition which contains two or more therapeutic or biologically active agents.

By "pharmaceutical preparation" or "pharmaceutical composition" is meant any composition which contains at least one therapeutically or biologically active agent and is suitable for administration to a patient. For the purposes of this invention, pharmaceutical compositions suitable for delivering a therapeutic to the upper alimentary canal include, but are not limited to solutions and suspensions delivered either as an oral spray or rinse, pastes, gels, chewable tablets, sublingual, gingival, or buccal wafers and films, chewing gum, lozenges, and other compositions designed to be retained in the mouth for an extended period of time. Any of these formulations can be prepared by well known and accepted methods of art. See, for example, Remington: The Science and Practice of Pharmacy, $19^{th}$ edition, (ed. AR Gennaro), Mack Publishing Co., Easton, Pa., 1995.

By "microsphere" is meant a bioerodable polymeric pharmaceutical delivery device having a diameter of 5-100 μm and a hollow central core suitable for encapsulation of the therapeutic agent. Typically, the therapeutic agent is encapsulated at the time of microsphere formulation.

By "therapeutically effective amount" is meant an amount sufficient to provide medical benefit. When administering trefoil peptides to a human patient according to the methods described herein, a therapeutically effective amount is usually about 0.1-1000 mg of trefoil peptide per day. Preferably, the patient receives, 10 mg, 100 mg, 250 mg, or 750 mg of trefoil peptide each day. The total daily does can be divided into multiple individual doses.

By "upper alimentary canal" is meant the portion of the digestive system proximal to the cardiac sphincter (cardioesophageal sphincter) of the stomach. Specifically, the upper alimentary canal is meant to include the oral cavity and associated structures (e.g., the tongue, gingival and sublingual tissues, and the hard and soft palates) and the esophagus.

By "biologically active," when referring to a TP is meant any polypeptide that exhibits an activity common to naturally occurring trefoil peptides. An example of a biological activity common to the family of trefoil peptides is the ability to alter gastrointestinal motility in a mammal. Other biological activities include mucopolysaccharide binding, maintenance of the mucosa, and repair of mucosal integrity upon injury (see, for example, Taupin et al., Proc. Natl. Acad. Sci, USA, 97:799-804, 1999).

By "high stringency conditions" is meant any set of conditions that are characterized by high temperature and low ionic strength and allow hybridization comparable with those resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. See, e.g., F. Ausubel et al., in *Current Protocols in Molecular Biology*, John Wiley & Sons, New York, N.Y., 1998, hereby incorporated by reference. Other features and advantages of the invention will be apparent from the following detailed description, and from the claims.

By "isolated DNA" is meant DNA that is free of the genes which, in the naturally-occurring genome of the organism from which the given DNA is derived, flank the DNA. Thus, the term "isolated DNA" encompasses, for example, cDNA, cloned genomic DNA, and synthetic DNA.

By "treating" is meant administering a pharmaceutical composition for prophylactic and/or therapeutic purposes. The active ingredients of the pharmaceutical composition can treat the primary indication (i.e., epithelial lesion) or secondary symptoms (e.g., concomitant infection, pain, or inflammation).

By "analgesic" is meant an agent which relieves pain by elevating the pain threshold without significantly disturbing the consciousness of the patient.

By "antimicrobial agent" is meant any compound that alters the growth of bacteria or fungi cells, or viruses whereby growth is prevented, stabilized, or inhibited, or wherein the microbes are killed. In other words, the antimicrobial agents can be microbiocidal or microbiostatic.

By "thermal burn" is meant injury to or destruction of at least the epithelial cell layer caused by exposure to excessive temperature. Thermal burns of the upper alimentary canal are usually caused by ingestion of overly-heated foods and liquids, or inhalation of super-heated air. Thermal burns are meant to include, but are not limited to, burns classified as first degree, second degree, and third degree burns.

By "chemical burn" is meant injury to or destruction of at least the epithelial cell layer caused by exposure to noxious chemicals. Typically, chemical exposures of the upper alimentary canal are caused by inhalation or ingestion.

By "antineoplastic therapy" is meant any treatment regimen used to treat cancer. Typical antineoplastic therapies include chemotherapy and radiation therapy.

BRIEF DESCRIPTION OF DRAWINGS

FIGS. 1A-B show the amino acid sequence (Accession No. BAA95531; SEQ ID NO.:1) and cDNA sequence (GenBank Accession No. NM_003226; SEQ ID NO.:2) of human intestinal trefoil factor, respectively.

FIGS. 2A and 2B show the amino acid sequence (Accession No. NP_0032166; SEQ ID NO.:3) and cDNA sequence (SEQ ID NO.:4) of human pS2 protein, respectively.

FIGS. 3A and 3B show the amino acid sequence (Accession No. 1909187A; SEQ ID NO.:5) and cDNA sequence (SEQ ID NO.: 6) of human spasmolytic polypeptide (SP).

FIG. 4 is a multisequence alignment of trefoil domains (SEQ ID NOS.:7-10)/TFF1, SP/TFF2, and ITF/TFF3. X denotes any amino acid residue.

DETAILED DESCRIPTION

The invention provides methods and compositions useful for the treatment of a wide range of lesions of the upper alimentary canal. The trefoil peptide therapy of this invention is particularly useful for treating epithelial lesions of the oral and esophageal mucosa, tongue, and gingival tissue.

We have discovered that epithelial lesions of the upper alimentary canal including the oral and esophageal mucosa, tongue, and gingival tissue can be treated by local administration of trefoil peptides. Thus, trefoil peptide therapy, according to the methods of this invention, can be delivered in any pharmaceutical composition which is useful for delivering therapeutics to the upper alimentary canal.

Pharmaceutical Preparations

Oral Sprays, Rinses, and Emulsions

Spray systems are particularly useful for delivering therapeutics to the upper alimentary canal. Suitable spray delivery systems include both pressurized and non-pressurized (pump actuated) delivery devices. The trefoil peptide-containing solution, delivered as an oral spray, is preferably an aqueous solution; however, organic and inorganic components, emulsifiers, excipients, and agents that enhance the organoleptic properties (i.e., flavoring agents or odorants) may be included. Optionally, the solution may contain a preservative that prevents microbial growth (i.e., methyl paraben). Although water itself may make up the entire carrier, typical liquid spray formulations contain a co-solvent, for example, propylene glycol, corn syrup, glycerin, sorbitol solution and the like, to assist solubilization and incorporation of water-insoluble ingredients. In general, therefore, the compositions of this invention preferably contain from about 1-95% v/v and, most preferably, about 5-50% v/v, of the co-solvent. When prepared as an spray, patients typically self-administer 1-5 times per day. The spray delivery system is normally designed to deliver 50-100 µl per actuation, and therapy may require 1-5 actuations per dose. The rheological properties of the spray formulation are optimized to allow shear and atomization for droplet formation. Additionally, the spray delivery device is designed to create a droplet size which promotes retention on mucosal surfaces of the upper alimentary canal and minimize respiratory exposure.

Compositions suitable for oral sprays can also be formulated as an oral rinse or mouthwash. Administration of trefoil peptides using these formulations is typically done by swishing, gargling, or rinsing the oral cavity with the formulation. Optionally, these formulations can be swallowed, providing trefoil peptide therapy to the esophagus, stomach, and/or intestines. This delivery method is particularly useful for treating patients suffering related disorders of the intestinal epithelium. For example, patients receiving antineoplastic chemotherapy, in addition to oral mucositis, frequently develop more distal lesions of the gastrointestinal tract such as lesions of the gastric and intestinal epithelium. It is well known that trefoil peptides, particularly ITF, are stable at stomach pH. Thus, swallowing a trefoil peptide-containing solution designed primarily for treating oral mucositis may also benefit lesions of the lower alimentary canal (i.e., stomach and intestines).

In an alternative formulation, the trefoil peptides and/or other therapeutics can be encapsulated in bioerodable microspheres rather than being dissolved in the aqueous phase of the formulation. A wide variety of microencapsulation drug delivery systems have been developed and many share similar polymeric compositions as used for bioerodable films (described below). Polymers commonly used in the formation of microspheres include, for example, poly-ε-caprolactone, poly(ε-caprolactone-Co-DL-lactic acid), poly(DL-lactic acid), poly(DL-lactic acid-Co-glycolic acid) and poly(ε-caprolactone-Co-glycolic acid) (see, for example, Pitt et al., J. Pharm. Sci., 68:1534, 1979).

Microspheres can be made by procedures well known in the art including spray drying, coacervation, and emulsification (see for example Davis et al. Microsphere and Drug Therapy, Elsevier, 1984; Benoit et al. Biodegradable Microspheres: Advances in Production Technologies, Chapter 3, Ed. Benita, S, Dekker, New York, 1996; Microencapsulation and Related Drug Processes, Ed. Deasy, Dekker, 1984, New York; U.S. Pat. No. 6,365,187). Preferably, the microspheres are bioadhesive or are prepared in formulations containing a bioadhesive excipient.

Other technical features of the trefoil peptide-containing solutions are easily modified to suit the specific pharmaceutical formulation and the clinical indication being treated. For example, the pH and osmolality of the formulation may be adjusted to confer trefoil peptide stability, while minimizing oral irritancy and sensitivity.

Ointments, Pastes, and Gels

Lesions of the oral and esophageal epithelium caused by trauma are amenable to trefoil peptide therapy delivered as an ointment, paste, or gel. The viscous nature of these types of preparations allows for direct application into the wound site. Optionally, the wound site can be covered with a dressing to retain the trefoil peptide-containing composition, protect the lesion from trauma, and/or absorb exudate. As discussed further below, these preparations are particularly useful to restore epithelial integrity following traumatic surgical procedures such as, for example, tooth extraction, tissue biopsy, or a tumor resection. Such viscous formulations may also have a local barrier effect thereby reducing irritation and pain.

Mucoadhesives

A mucoadhesive excipient can be added to any of the previously described pharmaceutical compositions. The mucoadhesive formulations coat the upper alimentary canal providing protection, inhibiting irritation, and accelerating healing of inflamed or damaged tissue. Mucoadhesive formulations also promote prolonged contact of the trefoil peptide with the mucosal epithelium. Mucoadhesive formulations suitable for use in pharmaceutical preparations delivered by mouth are well known in the art (e.g., U.S. Pat. No. 5,458, 879). Particularly useful mucoadhesives are hydrogels composed of about 0.05-20% of a water-soluble polymer such as, for example, poly(ethylene oxide), poly(ethylene glycol), poly(vinyl alcohol), poly(vinyl pyrrolidine), poly(acrylic acid), poly(hydroxy ethyl methacrylate), hydroxyethyl ethyl cellulose, hydroxy ethyl cellulose, chitosan, and mixtures thereof. These polymeric formulations can also contain a dispersant such as sodium carboxymethyl cellulose (0.5-5.0%).

Other preferred mucoadhesive excipients for liquid compositions are ones that allow the composition to be administered as a flowable liquid but will cause the composition to gel in the upper alimentary canal, thereby providing a bioadhesive effect which acts to hold the therapeutic agents at the lesion site for an extended period of time. The anionic polysaccharides pectin and gellan are examples of materials which when formulated into a suitable composition will gel in the upper alimentary canal, owing to the presence of cations in the mucosal and salivary fluids. The liquid compositions containing pectin or gellan will typically consist of 0.01-20% w/v of the pectin or gellan in water or an aqueous buffer system.

Other useful compositions which promote mucoadhesion and prolonged therapeutic retention in the upper alimentary canal are colloidal dispersions containing 2-50% colloidal particles such as silica or titanium dioxide. Such formulations form as a flowable liquid with low viscosity suitable as a mouthwash or for generating a fine mist. However, the particles interact with glycoprotein, especially mucin, transforming the liquid into a viscous gel, providing effective mucoadhesion (e.g., U.S. Pat. Nos. 5,993,846 and 6,319,513).

Bioerodable Film Delivery Devices

The most simple bioerodable devices contain the therapeutic agent(s) incorporated into a solid, usually lipid-containing, film or tablet. The device is formulated to remain solid at room temperature, but melt at body temperature, releasing the incorporated therapeutics. Suitable formulations of this type include, for example, cocoa butter.

Polymeric film devices provide several advantages for therapeutic delivery to the oral cavity. Unlike rinses, pastes, gels, and other flowable compositions, a film device can reside for prolonged periods of time (i.e., hours to days) in the oral cavity and provide sustained release throughout its residency. Typically, the film is partially or completely bioerodable and contains a mucoadhesive layer to fasten the film to the oral mucosa. Film devices, in addition to its use for delivering therapeutics, can also provide protection against mechanical injury or microbial infection of a lesion site. This physical barrier function is particularly advantageous when treating conditions such as mucositis or aphthous stomatitis. Additionally, as discussed further below, a film device can be used to release trefoil peptide therapy directly onto the underlying mucosa, into the lumen of the oral cavity, or a combination of both.

Film devices consist of at least two layers; a mucoadhesive layer suitable for attaching the film to the oral mucosa and a bulk layer which contains the active therapeutic(s). Many suitable mucoadhesives are known in the art and are discussed above. Optionally, one or more therapeutics can also be provided in the adhesive layer.

The bulk layer of the composite delivery device may be made of one or more bioerodable polymeric materials. Suitable polymers include, for example, starch, gelatin, polyethylene glycol, polypropylene glycol, polyethylene oxide, copolymers of ethylene oxide and propylene oxide, copolymers of polyethylene glycol and polypropylene glycol, polytetramethylene glycol, polyether urethane, hydroxyethyl cellulose, ethyl cellulose, hydroxypropyl cellulose, hydroxypropylmethyl cellulose, alginate, collagen, polylactide, poly(lactide-co-glycolide) (PLGA), calcium polycarbophil, polyethymethacrylate, cellulose acetate, propylene glycol, polyacrylic acid, crosslinked polyacrylic acid, hydroxyethyl methacrylate/methyl methacrylate copolymer, silicon/ethyl cellulose/polyethylene glycol, urethane polyacrylate, polystyrene, polysulfone, polycarbonate, polyorthoesters, polyanhydrides, poly(amino acids), partially and completely hydrolyzed alkylene-vinyl acetate copolymers, polyvinyl chloride, polymers of polyvinyl acetate, polyvinyl alkyl ethers, styrene acrylonitrile copolymers, poly(ethylene terphthalate), polyalkylenes, poly(vinyl imidazole), polyesters and combinations of two or more of these polymers.

A particularly useful bulk layer polymer consists of PLGA and ethyl cellulose. PLGA is bioerodable and can be formulated to degrade over a wide range of conditions and rates. Ethyl cellulose is a water-insoluble polymer that can act as a plasticizer for the PLGA when a film is formed, but will be eroded in a bodily fluid. Due to its water-insolubility, it also has an effect on the degree and rate of swelling of the resultant film.

An optional third layer which is impermeable to the trefoil peptide can also be added to the wafer. Preferably, this barrier layer is also bioerodable. Suitable barrier layer polymers include ethyl cellulose, poly(acrylic acid), or other polyelectrolytes. In one configuration, the barrier layer is placed on the opposite side of the bulk layer relative to the adhesive layer, thereby directing the released therapeutic agent onto the contacted epithelium rather than being diluted in the lumenal fluid. This configuration is particularly useful for treating discrete lesions (i.e., mucositis or aphthous stomatitis) of the tongue, sublingual tissue, or buccal mucosa. In an alternative configuration of the film device, the barrier layer is placed between the bulk layer and the adhesive layer. This configuration directs therapeutic release into the lumen of the oral cavity and is useful for treating more diffuse lesions of the tongue, oral cavity, and esophagus. The configuration is also useful for delivering therapeutics which are cytotoxic when administered at high concentrations because it has the effect of shielding the underlying tissue from direct contact with the therapeutic-containing film.

Chewable Tablets, Lozenges, and Confectionaries

Preparing a trefoil peptide-containing composition as a chewable tablet, lozenge, or a confectionary such as chewing gum provides several advantages to traditional drug delivery vehicles. First, prolonged contact and sustained release at the target site (mouth and esophagus) is achieved. Second, such formulations often results in higher patient compliance, especially when administering trefoil peptides to children.

Formulations for chewable tablets are well known and typically contain a base of sugar, starch, or lipid and a flavoring agent. An exemplary formulation for a chewable tablet is provided below.

Chewable ITF Tablet Formulation (per tablet)
Intestinal trefoil factor—300 mg
Mannitol—675 mg
Microcrystalline cellulose—75 mg
Corn starch—30 mg
Calcium sterate—22 mg
Flavoring Agent (i.e., sodium saccharin or peppermint oil)

The incorporation of therapeutics into chewing gum and other confectionary style formulations is known in the art (e.g., U.S. Pat. No. 5,858,391).

Therapeutics Agents

Trefoil Peptides

The therapeutic trefoil peptide(s) are typically mammalian intestinal trefoil peptides. Preferably, human intestinal trefoil peptides are used; however, trefoil peptides from other species including rat, mouse, and non-human primate, may be used. Typically, the trefoil peptide is intestinal trefoil factor (ITF); however, spasmolytic polypeptide (SP), or pS2 are also useful. Particularly useful ITF fragments that retain biological activity include the polypeptide corresponding to amino acid residues 15-73 of SEQ ID NO:1 ($ITF_{15-73}$) and amino acid residues 21-73 of SEQ ID NO:1 ($ITF_{21-73}$). Other useful ITF fragments are formed following cleavage of the C-terminal phenylalanine residue (i.e., $ITF_{1-72}$, $ITF_{15-72}$, and $ITF_{21-72}$).

The trefoil peptides are present in the compositions of the invention at a concentration of between 0.1-1000 mg/ml, depending on the nature and condition of the lesion being treated, the anticipated frequency and duration of therapy, and the type of pharmaceutical composition used to deliver the trefoil peptide. Typically, therapy is designed to deliver 0.1-500 mg of trefoil peptide per day to the patient.

Anti-Inflammatory Agents

Any suitable anti-inflammatory agent can be formulated in the compositions of the invention, at concentrations known for these agents. Many of the most useful anti-inflammatory agents also have analgesic and/or antipyretic properties. Anti-inflammatory agents suitable for co-formulation with a trefoil peptide include, for example, acetaminophen, aspirin (acetylsalicylic acid), ibuprofen, phenylbutazone, indomethacin, sulindac, diclofenac, and naproxen.

Antimicrobial Agents

Any of the many known microbial agents can be used in the compositions of the invention at concentrations generally used for these agents. Antimicrobial agents include antibacterials, antifungals, antivirals, and other topical antiseptics.

Examples of antibacterial agents (antibiotics) include the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, and norfloxacin), and other antibiotics including chloramphenicol, clindamycin, cycloserine, isoniazid, rifampin, and vancomycin.

Antiviral agents are substances capable of destroying or suppressing the replication of viruses. Examples of anti-viral agents include 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon, adenine arabinoside, protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Antifungal agents include both fungicidal and fungistatic agents such as, for example, amphotericin B, butylparaben, clindamycin, econaxole, fluconazole, flucytosine, griseofulvin, nystatin, and ketoconazole.

Topical antiseptics include agents such as, for example, povidone-iodine and benzalkonium chloride.

Analgesics and Anesthetics

Any of the commonly used topical analgesics can be used in the compositions of the invention. The analgesic is present in an amount such that there is provided to the oral lesion a topical concentration of between one-half and five percent concentration for lidocaine (5-50 mg/ml in 20-40 ml per dose of liquid). Examples of other useful anesthetics include procaine, lidocaine, tetracaine, dibucaine, benzocaine, p-buthylaminobenzoic acid 2-(diethylamino) ethyl ester HCl, mepivacaine, piperocaine, and dyclonine.

Other analgesics include opioids such as, for example, morphine, codeine, hydrocodone, and oxycodone. Any of these analgesics may also be co-formulated with other compounds having analgesic or anti-inflammatory properties, such as acetaminophen, aspirin, and ibuprofen.

Steroids

Steroids are commonly used to treat lesions of the upper alimentary canal. For example, oral aphthous stomatitis is typically treated using a paste preparation of triamcinolone (0.1%), hydrocortisone, fluticasone, or beclomethasone.

Conditions of the Upper Alimentary Canal Treated Using Trefoil Peptides

Mucositis

Mucositis is a common condition of the oral cavity which is characterized by inflammation of the mucous membranes. The condition is frequently caused by antineoplastic therapy, including chemotherapy and local radiation therapy. Symptoms of mucositis include ulcerations, redness, and swelling, and is associated with epithelial cell injury and death. Patients suffering from severe mucositis are susceptible to dehydration and malnutrition because mucositis pain limits dietary intake. In severe cases, mucositis can be so debilitating that patients may require prolonged hospitalization, parenteral nutrition, and narcotic pain medication. Additionally, destruction of the mucosal epithelium increases a patient's susceptibility to local and systemic infection. Disruption of the barrier function permits entry of microorganisms and microbial products normally retained in the gut lumen. Thus, pharmaceutical preparations which reduce the adverse effects associated with chemotherapy will improve the patient's quality of life, compliance with self-medication, and may permit administration of higher chemotherapeutic doses. Typically, mucositis is treated using a trefoil peptide-containing rinse or oral spray which the patient self-administers 1-5 times per day. The aqueous solution preferably contains a mucoadhesive and an anti-inflammatory agent. Other therapeutics, such as an topical analgesic agent (e.g., lidocaine) may also be present. Alternatively, if the lesions are few in number and spatially localized, a trefoil peptide-containing film device an be placed directly over the lesions.

Tooth Extraction

Trefoil peptide-containing compositions of the invention are used to lessen complications and speed healing of the wound created by the extraction of a tooth. An oral rinse, paste, ointment, or gel, as described above, is applied to the site of extraction immediately following the procedure and then 1-4 times per day, as needed, until epithelial regrowth is complete. Preferably, a topical analgesic is included in the formulation to relieve the temporary discomfort cause by the trauma of extraction. As a prophylactic measure, antibiotic agents may also be included in the formulation.

Gingivitis

Gingivitis is most commonly a chronic disease requiring ongoing treatment, in some cases for months or even years. The trefoil peptide-containing compositions of the invention can be employed to treat gingivitis, alone or in conjunction with other treatments, particularly with an anti-microbial agent, and most commonly with an antibacterial agent. An oral trefoil peptide-containing rinse is swished in the patient's mouth at least once every 2-3 days, but as often as thrice daily, over a 3-4 week period, and the regimen is repeated as needed. Alternatively, the trefoil peptide is formulated into a gel or toothpaste. In severe cases, a viscous gel or ointment having a high trefoil peptide concentration is applied directly to the wound via a pledget with a stick applicator.

Trefoil peptide-containing compositions can also be delivered in biodegradable drug delivery systems capable of formation of films applied below the gum line (described in U.S. Pat. Nos. 5,945,115 and 5,990,194. A biodegradable polymer, admixed with the trefoil peptide, is provided where the polymer can be injected in as a free-flowing solution below the gum line using a syringe. The polymer solution then, in situ, forms a solid biodegradable implant.

Aphthous Stomatitis

At the first indication of an outbreak of aphthous stomatitis (generally, the first twinge of pain), the patient swishes the mouth with a trefoil peptide-containing rinse, 1-4 times per day until the ulcer heals (generally 5-10 days). A trefoil peptide-containing gel can also be applied to the ulcer, in the same manner that steroid-containing gels are currently used. In addition, a gel can contain both a trefoil protein and a steroid known to be effective for aphthous stomatitis treatment. A direct application of more concentrated material can be directly applied to the wound via a pledget with a stick applicator. Alternatively, the lesion can be treated directly by applying a bioerodable film device containing both a trefoil peptide and a steroid (i.e., triamcinolone) directly to the lesion. Any formulation useful for treating aphthous stomatitis can also, optionally, contain a local anesthetic (i.e., lidocaine or benzocaine).

Behcet's Disease

Behcet's Disease is a rare, multi-system rheumatic disorder characterized by systemic vasculitis. One of the most frequent symptoms of Behcet's Disease is recurrent oral ulcerations which resemble aphthous lesions. Currently, treatment for Behcet's Disease is palliative,-not curative. Thus, the trefoil peptides can be used to treat lesions of the upper alimentary canal in conjunction with currently available Behcet's Disease therapies including, for example, interferon alpha 2A and 2B, levamisole, cyclosporine, cyclophosphamide, and colchicine.

Oral Biopsy and Oral Surgery

In cases in which an oral neoplasm is suspected or known to be malignant, a biopsy or a curative resection is performed using a needle or a scalpel, resulting in an open wound. The surgical area, susceptible to infection and inflammation, is treated by rinsing with a trefoil peptide-containing solution 1-4 times per day. Preferably, an analgesic, an anti-inflammatory, and an antibiotic are included in the formulation. Alternatively, a more concentrated gel, paste, or ointment may be directly applied to the lesion site. For post-operative treatment following resection of a malignancy, a topically active chemotherapeutic can be including in the trefoil peptide-containing composition.

Thermal and Chemical Burns

Trauma to the upper alimentary canal is frequently caused by exposure to excessive heat or noxious chemicals. Thermal burns to the upper alimentary canal are frequently mild in nature (i.e., first or second degree burns), resulting from the ingestion of overheated food or drink. More severe thermal burns of the oral mucosa and upper esophagus can be caused by inhalation of super heated air and are frequently observed in firefighters or victims of house or forest fires.

Chemical exposure can also damage the mucosa of the upper alimentary canal. Mild mucosal irritations and burns are often caused by ingestion of acidic food (i.e., fruits). More severe chemical burns are usually associated with accidental industrial or occupational exposures.

The trefoil peptide-containing pharmaceutical formulations described herein are useful for treating thermal and chemical burns of the upper alimentary canal. Preferably, viscous liquid or gel formulation containing a mucoadhesive is used to prolong mucosal exposure to the trefoil peptide. Alternatively, a sustained release formulation, such as a bioerodable film, is used. Topical analgesics and antimicrobial agents are the most preferred secondary therapeutics to be co-administered.

Production of Trefoil Peptides

Trefoil peptides can be produced by any method known in the art for expression of recombinant proteins. Nucleic acids that encode trefoil peptides may be introduced into various cell types or cell-free systems for expression thereby allowing large-scale production, purification, and patient therapy.

Eukaryotic and prokaryotic trefoil peptide expression systems may be generated in which a trefoil peptide gene sequence is introduced into a plasmid or other vector, which is then used to transform living cells. Constructs in which the trefoil peptide cDNA contains the entire open reading frame inserted in the correct orientation into an expression plasmid may be used for protein expression. Prokaryotic and eukaryotic expression systems allow for the expression and recovery of trefoil peptide fusion proteins in which the trefoil peptide is covalently linked to a tag molecule which facilitates identification and/or purification. An enzymatic or chemical cleavage site can be engineered between the trefoil peptide and the tag molecule so that the tag can be removed following purification.

Typical expression vectors contain promoters that direct the synthesis of large amounts of mRNA corresponding to the inserted trefoil peptide nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of a trefoil peptide nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector. Biologically active trefoil peptides also can be produced using a Pichia yeast expression system (see, for example, U.S. Pat. Nos. 4,882,279 and 5,122,465; hereby incorporated by reference).

Mammalian cells can also be used to express a trefoil peptide. Stable or transient cell line clones can be made using trefoil peptide expression vectors to produce the trefoil peptides in a soluble (truncated and tagged) form. Appropriate cell lines include, for example, COS, HEK293T, CHO, or NIH cell lines.

Once the appropriate expression vectors are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. In vitro expression of trefoil peptides, fusions, or polypeptide fragments encoded by cloned DNA may also be used. Those skilled in the art of molecular biology will understand that a wide variety of expression systems and purification systems may be used to produce recombinant trefoil peptides and fragments thereof. Some of these systems are described, for example, in Ausubel et al. (Current Protocols in Molecular Biology, John Wiley & Sons, New York, N.Y. 2000, hereby incorporated by reference).

Transgenic plants, plant cells and algae are also particularly useful for generating recombinant trefoil peptides for use in the methods and compositions of the invention. For example, transgenic tobacco plants or cultured transgenic tobacco plant cells expressing a trefoil peptide can be created using techniques known in the art (see, for example, U.S. Pat. Nos. 5,202,422 and 6,140,075). Transgenic algae expression systems can also be used to produce recombinant trefoil peptides (see, for example, Chen et al., Curr. Genet. 39:365-370, 2001).

Once a recombinant protein is expressed, it can be isolated from cell lysates using protein purification techniques such as affinity chromatography. Once isolated, the recombinant protein can, if desired, be purified further by e.g., high performance liquid chromatography (HPLC; e.g., see Fisher, Laboratory Techniques In Biochemistry And Molecular Biology, Work and Burdon, Eds., Elsevier, 1980).

Polypeptides of the invention, particularly short trefoil peptide fragments can also be produced by chemical synthesis using, for example, Merrifield solid phase synthesis, solution phase synthesis, or a combination of both (see, for example, the methods described in Solid Phase Peptide Synthesis, 2nd ed., 1984, The Pierce Chemical Co., Rockford, Ill.). Optionally, peptide fragments are then be condensed by standard peptide assembly chemistry.

EXAMPLE 1

Mucositis Treatment for Patients Receiving Antineoplastic Therapy

Trefoil peptide therapy is initiated prior to antineoplastic therapy (i.e., chemotherapy or radiation therapy), as a prophylactic to delay or prevent the onset of mucositis. Preferably, the patient begins trefoil peptide therapy three days prior to the first dose of antineoplastic therapy. During the prophylactic stage, the patient rinses the oral cavity with a trefoil peptide-containing solution. Alternatively, for convenience, the trefoil peptide is provided as a concentrated oral spray. Preferably, the patient swallows the solution, providing protection for the epithelial cells of the esophagus and lower gastrointestinal tract. Rinsing with and swallowing the trefoil peptide-containing solution continues at least twice daily until oral or esophageal mucositis is detected.

In patients with existing mucositis, epithelial healing is promoted using trefoil peptide therapy as described above. Palliative therapy is provided using benzocaine (a local anesthetic), and nystatin (an antifungal). The trefoil peptide can be co-formulated with the benzocaine and nystatin. For example, the patient swishes an oral rinse solution (mouthwash), containing all therapeutic agents, 1-5 times each day. Alternatively, the trefoil peptide can be provided in a concentrated oral spray, with or without benzocaine and the nystatin is administered in an oral rinse.

The oral rinse solutions can either be swallowed or spit out. If swallowed, an antacid may also be included in the formulation. Other useful therapeutics which provide palliative therapy include anti-inflammatories (e.g., ibuprofen) and other anti-microbial agents. Exemplary oral rinses useful for treating chemotherapy-induced mucositis are provided below, but are not intended to be limiting. A skilled physician or pharmacist will immediately recognize appropriate substitutions, additions, and deletions that can be made to these formulations.

Rinse#1: Mix equal parts of:
(i) diphenhydramine elixir (Benadryl®)
(ii) kaolin-pectin suspension (Kaopectate(®)
(iii) viscous lidocaine HCl (2%)
(iv) nystatin (oral suspension; 100,000 iu/ml)
(v) ITF (2.5 mg/ml)
preferably swallowed after swishing Rinse#2: Mix equal parts of:
(i) diphenhydramine elixir (Benadryl®)
(ii) Maalox® (MgOH & AlOH; 40 mg/ml)
(iii) viscous lidocaine HCl (2%)
(iv) ITF (2.5 mg/ml)
preferably swallowed after swishing Other Embodiments All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting occurrence or expansion of ulcerative oral lesions in a human patient having oral mucositis comprising orally administering to said patient a therapeutic composition comprising human ITF (intestinal trefoil factor) in an amount effective to inhibit occurrence or expansion of said ulcerative oral lesions.

2. The method of claim 1, wherein said oral mucositis is caused by antineoplastic chemotherapy.

3. The method of claim 1, wherein said oral mucositis is caused by antineoplastic radiation therapy.

4. The method of claim 1, wherein said therapeutic composition is administered to said patient during or within three days prior to a course of antineoplastic chemotherapy.

5. The method of claim 1, wherein said therapeutic composition is administered to said patient during or within three days prior to a course of antineoplastic radiation therapy.

6. The method of claim 1, wherein said therapeutic composition is formulated as an oral spray.

7. The method of claim 6, wherein said oral spray is self-administered.

8. The method of claim 6, wherein said amount of human ITF effective to inhibit occurrence or expansion of said ulcerative oral lesions is between 10 and 250 milligrams daily.

9. The method of claim 8, wherein said therapeutic composition is administered in multiple individual daily doses.

10. The method of claim 1, wherein said therapeutic composition comprises a mucoadhesive excipient.

11. The method of claim 1, wherein said human ITF is in dimeric form.

12. The method of claim 1, further comprising administering to said patient a second therapeutic, wherein said human ITF and said second therapeutic are administered within 14 days of each other.

13. The method of claim 12, wherein said second therapeutic is an anti-inflammatory agent, an antibacterial agent, an anti-fungal agent, an anti-viral agent, or an analgesic.

14. The method of claim 13, wherein said antibacterial agent is a tetracycline.

15. The method of claim 13, wherein said anti-fungal agent is nystatin.

16. The method of claim 13, wherein said anti-viral agent is acyclovir.

17. The method of claim 13, wherein said analgesic is lidocaine.

18. The method of claim 12, wherein said human ITF and said second therapeutic are administered in the same formulation.

19. The method of claim 12, wherein said human ITF and said second therapeutic are administered in different formulations.

20. The method of claim 12, wherein said human ITF and said second therapeutic are administered within 24 hours of each other.

* * * * *

SEQUENCE LISTING

<160> NUMBER OF SEQ ID NOS: 10

<210> SEQ ID NO 1
<211> LENGTH: 73
<212> TYPE: PRT

<213> ORGANISM: Homo sapiens

<400> SEQUENCE: 1

Met Leu Gly Leu Val Leu Ala Leu Leu Ser Ser Ser Ala Glu Glu
1               5                   10                  15

Tyr Val Gly Leu Ser Ala Asn Gln Cys Ala Val Pro Ala Lys Asp Arg
            20                  25                  30

Val Asp Cys Gly Tyr Pro His Val Thr Pro Lys Glu Cys Asn Asn Arg
        35                  40                  45

Gly Cys Cys Phe Asp Ser Arg Ile Pro Gly Val Pro Trp Cys Phe Lys
    50                  55                  60

Pro Leu Gln Glu Ala Glu Cys Thr Phe
65                  70

<210> SEQ ID NO 2
<211> LENGTH: 222
<212> TYPE: DNA
<213> ORGANISM: Homo sapiens

<400> SEQUENCE: 2
atgctggggc tggtcctggc cttgctgtcc tccagctctg ctgaggagta cgtgggcctg      60
tctgcaaacc agtgtgccgt gccagccaag gacagggtgg actgcggcta cccccatgtc    120
acccccaagg agtgcaacaa ccggggctgc tgctttgact ccaggatccc tggagtgcct    180
tggtgtttca gcccctgca ggaagcagaa tgcaccttct ga                         222

<210> SEQ ID NO 3
<211> LENGTH: 84
<212> TYPE: PRT
<213> ORGANISM: Homo sapiens

<400> SEQUENCE: 3

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe

<210> SEQ ID NO 4
<211> LENGTH: 255
<212> TYPE: DNA
<213> ORGANISM: Homo sapiens

<400> SEQUENCE: 4
atggccacca tggagaacaa ggtgatctgc gccctggtcc tggtgtccat gctggccctc      60
ggcaccctgg ccgaggccca gacagagacg tgtacagtgg ccccccgtga aagacagaat    120
tgtggttttc ctggtgtcac gccctcccag tgtgcaaata agggctgctg tttcgacgac    180
accgttcgtg gggtcccctg gtgcttctat cctaatacca tcgacgtccc tccagaagag    240
gagtgtgaat tttag                                                      255

<210> SEQ ID NO 5
<211> LENGTH: 106
<212> TYPE: PRT
<213> ORGANISM: Homo sapiens

<400> SEQUENCE: 5

```
Glu Lys Pro Ser Pro Cys Gln Cys Ser Arg Leu Ser Pro His Asn Arg
 1               5                  10                  15

Thr Asn Cys Gly Phe Pro Gly Ile Thr Ser Asp Gln Cys Phe Asp Asn
            20                  25                  30

Gly Cys Cys Phe Asp Ser Ser Val Thr Gly Val Pro Trp Cys Phe His
        35                  40                  45

Pro Leu Pro Lys Gln Glu Ser Asp Gln Cys Val Met Glu Val Ser Asp
50                  55                  60

Arg Arg Asn Cys Gly Tyr Pro Gly Ile Ser Pro Glu Glu Cys Ala Ser
65                  70                  75                  80

Arg Lys Cys Cys Phe Ser Asn Phe Ile Phe Glu Val Pro Trp Cys Phe
                85                  90                  95

Phe Pro Asn Ser Val Glu Asp Cys His Tyr
            100                 105
```

<210> SEQ ID NO 6
<211> LENGTH: 390
<212> TYPE: DNA
<213> ORGANISM: Homo sapiens

<400> SEQUENCE: 6

```
atgggacggc gagacgccca gctcctggca gcgctcctcg tcctggggct atgtgccctg     60
gcggggagtg agaaaccctc ccctgccag tgctccaggc tgagccccca taacaggacg    120
aactgcggct ccctggaat caccagtgac cagtgttttg acaatggatg ctgtttcgac    180
tccagtgtca ctggggtccc ctggtgtttc caccccctcc caaagcaaga gtcggatcag    240
tgcgtcatgg aggtctcaga ccgaagaaac tgtggctacc cgggcatcag ccccgaggaa    300
tgcgcctctc ggaagtgctg cttctccaac ttcatctttg aagtgccctg gtgcttcttc    360
ccgaagtctg tggaagactg ccattactaa                                     390
```

<210> SEQ ID NO 7
<211> LENGTH: 41
<212> TYPE: PRT
<213> ORGANISM: Artificial Sequence
<220> FEATURE:
<223> OTHER INFORMATION: based on Homo sapiens
<220> FEATURE:
<221> NAME/KEY: VARIANT
<222> LOCATION: 1, 41
<223> OTHER INFORMATION: Xaa = Any Amino Acid

<400> SEQUENCE: 7

```
Xaa Cys Thr Val Ala Pro Arg Glu Arg Gln Asn Cys Gly Phe Pro Gly
 1               5                  10                  15

Val Thr Pro Ser Gln Cys Ala Asn Lys Gly Cys Cys Phe Asp Asp Thr
            20                  25                  30

Val Arg Gly Val Pro Trp Cys Phe Xaa
        35                  40
```

<210> SEQ ID NO 8
<211> LENGTH: 42
<212> TYPE: PRT
<213> ORGANISM: Artificial Sequence
<220> FEATURE:

```
<223> OTHER INFORMATION: based on Homo sapiens
<220> FEATURE:
<221> NAME/KEY: VARIANT
<222> LOCATION: 1, 42
<223> OTHER INFORMATION: Xaa = Any Amino Acid

<400> SEQUENCE: 8

Xaa Cys Ser Arg Leu Ser Pro His Asn Arg Thr Asn Cys Gly Phe Pro
 1               5                  10                  15

Gly Ile Thr Ser Asp Gln Cys Phe Asp Asn Gly Cys Cys Phe Asp Ser
             20                  25                  30

Ser Val Thr Gly Val Pro Trp Cys Phe Xaa
         35                  40

<210> SEQ ID NO 9
<211> LENGTH: 41
<212> TYPE: PRT
<213> ORGANISM: Artificial Sequence
<220> FEATURE:
<223> OTHER INFORMATION: based on Homo sapiens
<220> FEATURE:
<221> NAME/KEY: VARIANT
<222> LOCATION: 1, 41
<223> OTHER INFORMATION: Xaa = Any Amino Acid

<400> SEQUENCE: 9

Xaa Cys Val Met Glu Val Ser Asp Arg Arg Asn Cys Gly Tyr Pro Gly
 1               5                  10                  15

Ile Ser Pro Glu Glu Cys Ala Ser Arg Lys Cys Cys Phe Ser Asn Phe
             20                  25                  30

Ile Phe Glu Val Pro Trp Cys Phe Xaa
         35                  40

<210> SEQ ID NO 10
<211> LENGTH: 41
<212> TYPE: PRT
<213> ORGANISM: Artificial Sequence
<220> FEATURE:
<223> OTHER INFORMATION: based on Homo sapiens
<220> FEATURE:
<221> NAME/KEY: VARIANT
<222> LOCATION: 1, 41
<223> OTHER INFORMATION: Xaa = Any Amino Acid

<400> SEQUENCE: 10

Xaa Cys Ala Val Pro Ala Lys Asp Arg Val Asp Cys Gly Tyr Pro His
 1               5                  10                  15

Val Thr Pro Lys Glu Cys Asn Asn Arg Gly Cys Cys Phe Asp Ser Arg
             20                  25                  30

Ile Pro Gly Val Pro Trp Cys Phe Xaa
         35                  40
```